US008288477B2

(12) United States Patent
Hadba et al.

(10) Patent No.: US 8,288,477 B2
(45) Date of Patent: Oct. 16, 2012

(54) BIOABSORBABLE COMPOUNDS AND COMPOSITIONS CONTAINING THEM

(75) Inventors: Ahmad R. Hadba, Wallingford, CT (US); John Kennedy, Guilford, CT (US); Nadya Belcheva, Middletown, CT (US); Jon T. Reinprecht, Watertown, CT (US); Sajida S. Faroogi, Hamden, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 968 days.

(21) Appl. No.: 11/635,349

(22) Filed: Dec. 6, 2006

(65) Prior Publication Data

US 2007/0129505 A1    Jun. 7, 2007

Related U.S. Application Data

(60) Provisional application No. 60/742,941, filed on Dec. 6, 2005.

(51) Int. Cl.
*C08L 75/00* (2006.01)

(52) U.S. Cl. ........ 525/131; 525/130; 525/453; 525/458; 528/59; 528/73; 523/118

(58) Field of Classification Search .................. 525/131, 525/130, 458; 528/59, 73
See application file for complete search history.

(56) References Cited

U.S. PATENT DOCUMENTS

| | | | |
|---|---|---|---|
| 3,631,138 A | 12/1971 | Peters | |
| 3,773,595 A | 11/1973 | Burba et al. | |
| 3,879,493 A | 4/1975 | Mudde | |
| 3,903,232 A | 9/1975 | Wood et al. | |
| 3,976,055 A | 8/1976 | Monter et al. | |
| 4,057,535 A | 11/1977 | Lipatova et al. | |
| 4,061,662 A | 12/1977 | Marans et al. | |
| 4,132,839 A | 1/1979 | Marans et al. | |
| 4,169,175 A | 9/1979 | Marans et al. | |
| 4,321,350 A | 3/1982 | Lehmann | |
| 4,323,491 A | 4/1982 | Veselovsky et al. | |
| 4,404,296 A | 9/1983 | Schapel | |
| 4,425,472 A | 1/1984 | Howard et al. | |
| 4,451,627 A | 5/1984 | Frisch, Jr. et al. | |
| 4,477,604 A | 10/1984 | Oechsle, III | |
| 4,511,626 A | 4/1985 | Schumacher | |
| 4,547,561 A | 10/1985 | Wegner | |
| 4,654,409 A | 3/1987 | Shirai et al. | |
| 4,681,934 A | 7/1987 | Shibanai et al. | |
| 4,762,899 A | 8/1987 | Shikinami | |
| 4,722,815 A | 2/1988 | Shibanai | |
| 4,740,534 A | 4/1988 | Matsuda et al. | |
| 4,743,632 A | 5/1988 | Marinovic | |
| 4,804,691 A * | 2/1989 | English et al. ................ 523/118 |
| 4,806,614 A | 2/1989 | Matsuda et al. | |
| 4,829,099 A | 5/1989 | Fuller et al. | |
| 4,883,837 A | 11/1989 | Zabrocki | |
| 4,994,208 A | 2/1991 | McBain et al. | |
| 4,994,542 A | 2/1991 | Matsuda et al. | |
| 4,997,656 A | 3/1991 | Shikinami et al. | |
| 5,065,752 A | 11/1991 | Sessions et al. | |
| 5,082,663 A | 1/1992 | Konishi et al. | |
| 5,104,959 A * | 4/1992 | Hess et al. ........................ 528/79 |
| 5,166,300 A | 11/1992 | Rumon et al. | |
| 5,169,720 A | 12/1992 | Braatz et al. | |
| 5,173,301 A | 12/1992 | Itoh et al. | |
| 5,175,228 A | 12/1992 | Wang et al. | |
| 5,204,110 A | 4/1993 | Cartmell et al. | |
| 5,346,981 A | 9/1994 | Sarpeshkar et al. | |
| 5,374,704 A | 12/1994 | Muller et al. | |
| 5,384,333 A | 1/1995 | Davis et al. | |
| 5,389,718 A | 2/1995 | Potter et al. | |
| 5,457,141 A | 10/1995 | Matsuda | |
| 5,462,536 A | 10/1995 | Braatz et al. | |
| 5,574,104 A * | 11/1996 | Kolycheck et al. ........... 525/130 |
| 5,574,123 A | 11/1996 | Bock et al. | |
| 5,578,662 A | 11/1996 | Bennett et al. | |
| 5,603,798 A | 2/1997 | Bhat | |
| 5,626,863 A | 5/1997 | Hubbell et al. | |
| 5,672,652 A | 9/1997 | Bhat | |
| 5,688,860 A | 11/1997 | Croft | |
| 5,702,717 A | 12/1997 | Cha et al. | |
| 5,703,158 A | 12/1997 | Duan et al. | |
| 5,717,030 A | 2/1998 | Dunn et al. | |
| 5,780,573 A | 7/1998 | Iwata et al. | |
| 5,791,352 A | 8/1998 | Reich et al. | |
| 5,795,633 A | 8/1998 | Yokoyama et al. | |
| 5,869,566 A | 2/1999 | Thomas | |
| 5,874,500 A | 2/1999 | Rhee et al. | |
| 5,900,473 A | 5/1999 | Acevedo et al. | |
| 5,912,193 A | 6/1999 | Iwata et al. | |
| 5,922,809 A | 7/1999 | Bhat et al. | |
| 5,948,427 A | 9/1999 | Yamamoto et al. | |
| 5,976,305 A | 11/1999 | Bhat et al. | |
| 5,990,237 A | 11/1999 | Bentley et al. | |

(Continued)

FOREIGN PATENT DOCUMENTS

| | | |
|---|---|---|
| EP | 0 077 192 A2 | 4/1983 |
| EP | 0108933 A | 5/1984 |
| EP | 0295055 A | 12/1988 |
| EP | 0 482 467 A2 | 4/1992 |
| EP | 0 488 629 A1 | 6/1992 |
| EP | 0 301 516 B1 | 9/1992 |
| EP | 0 737 703 A2 | 10/1996 |
| EP | 1 391 205 A1 | 2/2005 |
| EP | 1 719 530 A | 11/2006 |
| GB | 985 144 | 3/1965 |

(Continued)

OTHER PUBLICATIONS

International Search Report from PCT/US06/47013 dated Oct. 3, 2007.
International Search Report from PCT/US06/46558 dated Nov. 9, 2007.
International Search Report from PCIIUS06/46552 dated Nov. 15, 2007.

(Continued)

*Primary Examiner* — Alicia Toscano

(57) ABSTRACT

Flowable bioabsorbable compounds are provided which are useful in producing surgical adhesive or sealant compositions.

21 Claims, No Drawings

U.S. PATENT DOCUMENTS

| | | | |
|---|---|---|---|
| 6,071,530 | A | 6/2000 | Polson |
| 6,103,850 | A | 8/2000 | Reichel et al. |
| 6,154,089 | A | 11/2000 | Rombach |
| 6,162,241 | A | 12/2000 | Coury et al. |
| 6,197,915 | B1 | 3/2001 | Yamana et al. |
| 6,201,072 | B1 | 3/2001 | Rathi et al. |
| 6,211,249 | B1 | 4/2001 | Cohn et al. |
| 6,217,894 | B1 | 4/2001 | Sawhney et al. |
| 6,235,815 | B1 | 5/2001 | Loercks et al. |
| 6,261,544 | B1 | 7/2001 | Coury et al. |
| 6,283,933 | B1 | 9/2001 | D'Alessio et al. |
| 6,290,729 | B1 | 9/2001 | Sleplan et al. |
| 6,296,908 | B1 | 10/2001 | Reihs et al. |
| 6,297,349 | B1 | 10/2001 | Goldberg et al. |
| 6,312,725 | B1 | 11/2001 | Wallace et al. |
| 6,339,130 | B1 | 1/2002 | Bennett et al. |
| 6,352,710 | B2 | 3/2002 | Sawhney et al. |
| 6,395,112 | B1 | 5/2002 | Sitzmann et al. |
| 6,395,823 | B1 | 5/2002 | Brink et al. |
| 6,461,631 | B1 | 10/2002 | Dunn et al. |
| 6,465,001 | B1 | 10/2002 | Hubbell et al. |
| 6,465,004 | B1 | 10/2002 | Rossi-Montero et al. |
| 6,495,127 | B1 | 12/2002 | Wallace et al. |
| 6,512,033 | B1 | 1/2003 | Wu |
| 6,521,717 | B1 | 2/2003 | Itoh |
| 6,551,610 | B2 | 4/2003 | Shalaby et al. |
| 6,555,645 | B1 | 4/2003 | Ikeda et al. |
| 6,565,969 | B1 | 5/2003 | Lamon et al. |
| 6,576,702 | B2 | 6/2003 | Anderle et al. |
| 6,579,952 | B1 | 6/2003 | Niki et al. |
| 6,582,713 | B2 | 6/2003 | Newell et al. |
| 6,592,899 | B2 | 7/2003 | Fowers et al. |
| 6,605,666 | B1 | 8/2003 | Scholz et al. |
| 6,723,114 | B2 | 4/2004 | Shalaby |
| 6,824,703 | B2 | 11/2004 | Lawrey et al. |
| 7,291,063 | B2 * | 11/2007 | Swisher et al. ............... 451/533 |
| 2002/0028875 | A1 | 3/2002 | Anderle et al. |
| 2003/0032734 | A1 | 2/2003 | Roby |
| 2003/0035786 | A1 | 2/2003 | Hendriks et al. |
| 2003/0044380 | A1 | 3/2003 | Zhu et al. |
| 2003/0176615 | A1 | 9/2003 | Lawrey et al. |
| 2003/0195293 | A1 | 10/2003 | Lubnin et al. |
| 2004/0019178 | A1 | 1/2004 | Gross et al. |
| 2004/0023842 | A1 | 2/2004 | Pathak et al. |
| 2004/0068078 | A1 | 4/2004 | Milbocker |
| 2004/0198901 | A1 | 10/2004 | Graham et al. |
| 2004/0198944 | A1 | 10/2004 | Meltzer et al. |
| 2004/0242831 | A1 | 12/2004 | Tian et al. |
| 2004/0259968 | A1 | 12/2004 | Krebs |
| 2005/0004661 | A1 | 1/2005 | Lewis et al. |
| 2005/0008672 | A1 * | 1/2005 | Winterbottom et al. ....... 424/423 |
| 2005/0069573 | A1 | 3/2005 | Cohn et al. |
| 2005/0070913 | A1 | 3/2005 | Milbocker et al. |
| 2005/0129733 | A1 | 6/2005 | Milbocker et al. |
| 2005/0131192 | A1 | 6/2005 | Matsuda et al. |
| 2005/0142162 | A1 | 6/2005 | Hunter et al. |
| 2005/0147647 | A1 | 7/2005 | Glauser et al. |
| 2005/0154148 | A1 | 7/2005 | Nakamichi et al. |
| 2005/0266086 | A1 | 12/2005 | Sawhney |
| 2007/0128152 | A1 | 6/2007 | Hadba et al. |
| 2007/0135605 | A1 | 6/2007 | Hadba et al. |
| 2007/0135606 | A1 | 6/2007 | Belcheva et al. |

FOREIGN PATENT DOCUMENTS

| | | |
|---|---|---|
| GB | 1 143 309 | 2/1969 |
| GB | 1 187 362 | 4/1970 |
| JP | 6263850 | 9/1994 |
| JP | 2002060341 | 2/2002 |
| WO | WO9419384 A | 9/1994 |
| WO | WO9902168 A | 1/1999 |
| WO | WO 00/43050 A1 | 7/2000 |
| WO | WO 01/00246 A | 1/2001 |
| WO | WO 01/16210 A | 3/2001 |
| WO | WO 03/011173 A2 | 2/2003 |
| WO | WO 03/011173 A3 | 2/2003 |
| WO | WO 2004/039323 A2 | 5/2004 |
| WO | WO 2004/039323 A3 | 5/2004 |
| WO | WO 2004/039857 A1 | 5/2004 |
| WO | WO 2004/041890 A1 | 5/2004 |
| WO | WO 2007/067623 A | 6/2007 |

OTHER PUBLICATIONS

International Search Report from PCT/US06/47023 dated Nov. 21, 2007.
European Search Report (EP 06 00 9170).
Margolin A L et al.: "Steroselective Oligomerizations Catalyzed by Lipases in Organic Olvents"; Tetrahedron Letters, vol. 28, No. 15, 1987pp. 1607-1610.
Okumura S. et al.: "Synthesis of Ester Oligomer by AspergillNiger Lipase" Agricultural and Biological Chemistry, vol. 48, No. 11, 1984, pp. 2805-2808.
Lumann N R et al.: The convergent Synthesis of Poly(glycerol-succininc acid) Dendritic Marcomolecules: Chemistry—A European Journal, VCH Publishers, US vol. 9, 2003, pp. 5618-5626.
Database WPI, Section Ch, Week 199442 Derwent Publications Ltd. London, GB; AN 1994-3383493.
Nivasu V M et al.: "In Situ Polymerizable Polyethyleneglycol Containing Polyesterpolyol Acrylates for Tissue Sealant Applications"; Biomaterials 2004 United Kingdom, vol. 25, No. 16, 2004, pp. 3283-3291.
Moon S-Y et al.: Polyurethane/Montorillonite Nancomposites Prepared From Crystalline Polyols, Using 1, 4-Butanediol and Organoclay Hybrids as Chain Extenders: European Polymer Journal, Pergamon Press Ltd. Oxford, GB,; vol. 40, No. 8, Aug. 2004; pp. 1615-16213.
M. J. Song, et al.: "Thermosensitive Sol-Gel Transition Behaviors of Poly(ethylene oide)/ Aliphatic Polyester/Poly(ethylene Oxide) Aqueous Solutions"; Journal of Polymer Science Part A: Polymer Chemistry, vol. 42, No. 3.; Feb. 1, 2004; pp. 772-784.
Mei Xuan Xu et al.: Synthesis and Properties of Unsaturated Polyester Dio-Polyurethanehybrid Polymer Network: Journal of Applied Polymer Science, John Wiley and Sons Inc. New York, US , vol. 54, No. 11, Dec. 12, 1994, pp. 1659-1663.
Oprea S. et al.: "Poly(urethane-methacrylates)s. Synthesis and Characterization"; Polymer, Elsevier Science Publishers B.V., GB, vol. 42, No. 17, Aug. 2001, pp. 7257-7266.
Hermanson, Greg T. "Bioconjugate Techniques" pp. 609-618 (1995).
International Search Report from Application EP 07 00 1213 dated Sep. 6, 2007.
International Search Report from Application EP 03 77 9244 dated Sep. 26, 2007.
International Search Report from Application PCT/US2006/46553 dated Oct. 31, 2007.
International Search Report from Application PCT/US2006/46554 dated Oct. 31, 2007.
International Search Report from Application No. PCT/US08/60971 dated Jul. 18, 2008.
Ferreira, et al., "Modification of the Biopolymer Castor Oil With Free Isocyanate Groups to Be Applied As Bioadhesive", *International Journal of Biological Macromolecules*, vol. 40, No. 2, pp. 144-152 (2007).
Ferreira, et al., "Development of a Biodegradable Bioadhesive Containing Urethane Groups", *Journal of Materials Science: Materials in Medicine*, vol. 19, No. 1, pp. 111-120 (2008).
European Search Report for Appln. No. EP 08 25 3645 mailed Mar. 5, 2009.
European Search Report for Appln. No. EP 08 25 3647 completed Mar. 6, 2009.
European Search Report for Appln. No. EP 08 25 1790.5 completed Jun. 19, 2009.
European Search Report for EP 06844893.5-2102 date of completion is Feb. 15, 2010 (3 pages).

* cited by examiner

BIOABSORBABLE COMPOUNDS AND COMPOSITIONS CONTAINING THEM

CROSS-REFERENCE TO RELATED APPLICATIONS

This application claims the benefit of U.S. Provisional Patent Application No. 60/742,941 filed Dec. 6, 2005, the entire disclosure of which is incorporated by reference herein.

BACKGROUND

1. Technical Field

This disclosure relates to flowable bioabsorbable compounds that are useful in making surgical adhesive or sealant compositions.

2. Background of Related Art

In recent years there has developed increased interest in replacing or augmenting sutures with adhesive bonds. The reasons for this increased interest include: (1) the potential speed with which repair might be accomplished; (2) the ability of a bonding substance to effect complete closure, thus preventing seepage of fluids; and (3) the possibility of forming a bond without excessive deformation of tissue.

Studies in this area, however, have revealed that in order for surgical adhesives to be accepted by surgeons, they must possess a number of properties. They must exhibit high initial tack and an ability to bond rapidly to living tissue; the strength of the bond should be sufficiently high to cause tissue failure before bond failure; the adhesive should form a bridge, typically a permeable flexible bridge; and the adhesive bridge and/or its metabolic products should not cause local histotoxic or carcinogenic effects.

Several materials useful as tissue adhesives or tissue sealants are currently available. One type of adhesive that is currently available is a cyanoacrylate adhesive. However, cyanoacrylate adhesives can have a high flexural modulus which can limit their usefulness. Another type of tissue sealant that is currently available utilizes components derived from bovine and/or human sources. For example, fibrin sealants are available. However, as with any natural material, variability in the material can be observed.

It would be desirable to provide a fully synthetic biological adhesive or sealant that is flexible, biocompatible and highly consistent in its properties. It would also be desirable if the adhesive or sealant was of sufficiently low viscosity to be sprayed.

SUMMARY

Bioabsorbable compounds are provided of the following formula (I):

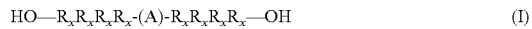
(I)

wherein A is a group derived from a dihydroxy compound with a molecular weight of less than 1000; R can be the same or different at each occurrence and can be groups derived from absorbable monomers; and x can be the same or different at each occurrence and is 0 or 1, provided that at least two R groups are present. The R groups can be derived from bioabsorbable monomers such as glycolide, lactide, p-dioxanone, ε-caprolactone, trimethylene carbonate and optionally combinations thereof.

Methods of making a compound of formula (I) are also contemplated wherein a dihydroxy compound is reacted with a bioabsorbable polymer under transesterifying conditions.

The compound of formula I can be functionalized with either electrophilic or nucleophilic groups to provide a compound of the following formula (II):

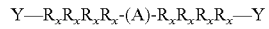

wherein Y is a group providing electrophilic or nucleophilic functionality; A is a group derived from a dihydroxy compound with a molecular weight of less than 1000; R can be the same or different at each occurrence and can be groups derived from absorbable monomers; and x can be the same or different at each occurrence and is 0 or 1, provided that at least two R groups are present. The nucleophilic functional groups can be, for example, $-NH_2$, $-SH$, $-OH$, $-PH_2$, $-CO-NH-NH_2$, or optionally mixtures thereof. The electrophilic functional groups can be, for example, $-CO_2N(COCH_2)_2$, $-CO_2H$, $-CHO$, $-CHOCH_2$, $-N=C=O$, $-SO_2-CH=CH_2$, $-N(COCH)_2$, $-S-S-(C_5H_4N)$, or optionally mixtures thereof.

In some embodiments the compound of formula (I) may be functionalized with isocyanate groups, the resulting compound thus having the following formula (III):

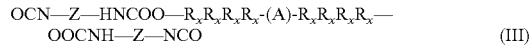
(III)

wherein Z is an aromatic or aliphatic group; A is a group derived from a dihydroxy compound with a molecular weight of less than 1000; R can be the same or different at each occurrence and can be groups derived from absorbable monomers; and x can be the same or different at each occurrence and is 0 or 1, provided that at least two R groups are present.

Methods of making a compound of formula (II) are also contemplated wherein a compound of formula (I) is reacted with a diisocyanate or a succinimidyl ester. The diisocyanate compound can be, for example, an aromatic diisocyanate, an aliphatic diisocyanate or an alicyclic diisocyanate. The succinimidyl ester can be, for example, a sulfosuccinimidyl ester or a N-hydroxysuccinimidyl ester.

In another aspect, a two part adhesive system is contemplated which includes a first component containing a functionalized compound of formula (II) and a second component containing a multifunctional compound. Where the functionalized compound of the first component includes electrophilic groups, the second component should contain compounds with multiple nucleophilic groups. Where the functionalized compound of the first component includes nucleophilic groups, the second component should contain compounds with multiple electrophilic groups. In particularly useful embodiments, where the first component contains an isocyanate-functional compound of formula III, the second component of the two part adhesive or sealant contains a polyamine compound. In some embodiments, the two part adhesive system is sprayable.

In another aspect, the present disclosure contemplates an apparatus including a first chamber containing a first composition including a functionalized compound of formula (II), a second chamber containing a second composition including a multifunctional compound, and at least one outlet for dispensing the first and second compositions.

In another aspect, the present disclosure contemplates a method including the steps of providing a first composition including a functionalized compound of formula (II) in a first chamber, a second composition including a multifunctional compound in a second chamber, and dispensing the first and second compositions through at least one outlet. The first and second compositions can be dispensed simultaneously or sequentially. Alternatively, the first and second compositions can be mixed prior to being dispensed. In some embodiments the two compositions may be dispensed by spraying.

DETAILED DESCRIPTION OF PREFERRED EMBODIMENTS

Bioabsorbable compounds are provided herein. Rather than being solids, the compounds are flowable and in some embodiments of sufficiently low viscosity to be sprayable. The compounds can be functionalized and used in tissue adhesives and sealants. In some embodiments, the compounds are used as one component of a two component tissue adhesive or sealant. In particularly useful embodiments, the two part tissue adhesive or sealant is sprayable.

The bioabsorbable compounds described herein may have the formula (I):

$$\text{HO}-R_xR_xR_xR_x\text{-(A)-}R_xR_xR_xR_x-\text{OH} \qquad (I)$$

wherein A is a group derived from a dihydroxy compound with a molecular weight of less than about 1000; R can be the same or different at each occurrence and includes groups derived from absorbable monomers; and x can be the same or different at each occurrence and is 0 or 1, provided that at least two R groups are present.

The low molecular weight of the A group and limited number of R groups keeps the viscosity of the compound sufficiently low that the compound flows at temperatures at or below body temperature making the compound useful for forming sprayable adhesives. The present compounds can be flowable at the temperatures encountered in use. For example, flowable compositions may have a viscosity of from about 1,000 to about 500,000 centipoise at temperatures of from about 0° C. to about 40° C. Alternatively, the compounds can be sprayable at the temperatures encountered in use. For example, sprayable compositions may have a viscosity of from about 1,000 to about 150,000 centipoise at temperatures of from about 0° C. to about 40° C.

Suitable dihydroxy compounds from which the A group may be derived include, for example, polyols including polyalkylene oxides, polyvinyl alcohols, and the like. In some embodiments, the dihydroxy compounds can be a polyalkylene oxide such as polyethylene oxide ("PEO"), polypropylene oxide ("PPO"), or block or random copolymers of polyethylene oxide (PEO) and polypropylene oxide (PPO).

In one embodiment, a polyethylene glycol ("PEG") may be utilized as the dihydroxy compound. It may be desirable to utilize a PEG with a molecular weight ranging from about 200 to about 1000, typically from about 400 to about 900, in some embodiments about 600. Mixtures of PEG may also be used. Suitable PEGs include those commercially available from a variety of sources under the designations PEG 200, PEG 400, PEG 600 and PEG 900.

Monomers from which the bioabsorbable R groups can be derived include, for example, groups derived from glycolide, glycolic acid, lactide, lactic acid, ε-caprolactone, dioxanone, trimethylene carbonate, and mixtures thereof.

Thus, in embodiments, a bioabsorbable compound of the present disclosure may have a formula of

HO—R-(A)-R—OH or

HO—R—R-(A)-R—R—OH, or

HO—R—R—R-(A)-R—R—R—OH, wherein A and R are as defined above.

The compound can be made using conventional techniques. In some useful embodiments, the compound may be made by reacting a dihydroxy compound and a bioabsorbable polymer under transesterifying conditions. Suitable transesterification conditions include reacting the dihydroxy compound with the bioabsorbable polymer in the presence of a catalyst (e.g., stannous octoate) at temperatures of from about 100° C., in embodiments from about 120° C. to about 200° C. to about 220° C., for periods of time from about 1 hour to about 50 hours, in embodiments from about 10 hours to about 40 hours. As those skilled in the art will appreciate, transesterification is a reaction between an ester of one alcohol and a second alcohol to form an ester of the second alcohol and an alcohol from the original ester. Through transesterification, bioabsorbable linkages from the bioabsorbable polymer are transferred onto the dihydroxy compound. Given sufficient reaction time and controlled stoichiometry of the reactants, the resulting compound may possess a desired number of bioabsorbable linkages attached to each side of the dihydroxy compound. For example, starting with sufficient bioabsorbable polymer to provide a molar equivalent of ester groups that is twice the molar equivalent of hydroxyl groups on the dihydroxy compound will provide, on average, two bioabsorbable groups at each end of the dihydroxy compound.

The distribution of bioabsorbable linkages changes as a function of time after addition of the starting materials. This distribution has a marked effect on the properties of the compound. For example, the viscosity of the resulting compound can be adjusted by balancing the molecular weight of the dihydroxy compound and the number of bioabsorbable groups present on the compound.

In certain embodiments, the compounds of formula (I) can be functionalized in accordance with this disclosure. The functionalized compounds may be of the following formula (II):

$$Y-R_xR_xR_xR_x\text{-(A)-}R_xR_xR_xR_x-Y \qquad (II)$$

wherein Y is a group providing electrophilic or nucleophilic functionality; A is a group derived from a dihydroxy compound with a molecular weight of less than about 1000 as described above; R can be the same or different at each occurrence and includes groups derived from absorbable monomers as described above; and x can be the same or different at each occurrence and is 0 or 1, provided that at least two R groups are present. Illustrative examples of nucleophilic functional groups include, but are not limited to, —NH$_2$, —SH, —OH, —PH$_2$, —CO—NH—NH$_2$, and the like. Illustrative examples of electrophilic functional groups include, but are not limited to, —CO$_2$N(COCH$_2$)$_2$, —CO$_2$H, —CHO, —CHOCH$_2$, —N=C=O, —SO$_2$CH=CH$_2$, —N(COCH)$_2$, —S—S—(C$_5$H$_4$N), combinations thereof, and the like. Compounds suitable for reacting with the compound of formula I to provide such functionality will be apparent to those skilled in the art.

Compounds of formula II can be prepared using conventional techniques. For example, a compound of formula I may be reacted with a compound that provides the desired functional group. For example, to provide succinimidyl groups, the compound of formula I can be reacted with a succinimidyl ester, such as, for example, a sulfosuccinimidyl ester or a N-hydroxysuccinimidyl ester. The particular reaction conditions will depend on the particular starting materials. Examples of suitable reaction conditions include those set forth in Hermanson, Bioconjugate Techniques, pp. 609-618 (1996), the entire disclosure of which is incorporated by reference herein.

In particularly useful embodiments, isocyanate functionality may be provided on the compound by reacting a compound of formula I with a diisocyanate. In some embodiments, the resulting isocyanate-functionalized compound is of the following formula (III):

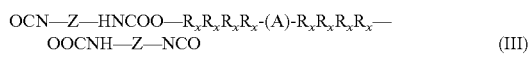
(III)

wherein Z is an aromatic or aliphatic group; A is a group derived from a dihydroxy compound with a molecular weight of less than 1000 as described above; R can be the same or different at each occurrence and includes groups derived from absorbable monomers as described above; and x can be the same or different at each occurrence and is 0 or 1, provided that at least two R groups are present.

In embodiments, the Z group may be toluene, diphenylmethane, diphenyldimethylmethane, dibenzyl, naphthylene, phenylene, xylylene, oxybisphenyl, tetramethylxylylene, tetramethylene, hexamethylene, lysine, methylpentane, trimethylhexamethylene, isophorone, cyclohexane, hydrogenated xylylene, hydrogenated diphenylmethane, hydrogenated trimethylxylylene, trimethylphenylene, and combinations thereof.

Suitable isocyanates for reaction with the compound of formula I include aromatic, aliphatic and alicyclic diisocyanates. Examples include, but are not limited to, aromatic diisocyanates such as 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, 4,4'-oxybis(phenylisocyanate) or tetramethylxylylene diisocyanate; aliphatic diisocyanates such as tetramethylene diisocyanate, hexamethylene diisocyanate, dimethyl diisocyanate, lysine diisocyanate, 2-methylpentane-1,5-diisocyanate, 3-methylpentane-1,5-diisocyanate or 2,2,4-trimethylhexamethylene diisocyanate; and alicyclic diisocyanates such as isophorone diisocyanate, cyclohexane diisocyanate, hydrogenated xylylene diisocyanate, hydrogenated diphenylmethane diisocyanate, hydrogenated trimethylxylylene diisocyanate, 2,4,6-trimethyl 1,3-phenylene diisocyanate or commercially available isocyanates sold under the name DESMODURS® from Bayer Material Science.

Methods for reacting the compound of formula I with a diisocyanate are within the purview of those skilled in the art. For example, the compound of formula I may be combined with a suitable diisocyanate, and heated to a suitable temperature from about 20° C. to about 150° C. in embodiments from about 30° C. to about 120° C. for periods of time from about 10 minutes to about 24 hours, in embodiments from about 1 hour to about 20 hours. The resulting diisocyanate-functional compound may then be recovered and purified by conventional means.

The functionalized compounds of formula II can be used as an ingredient in a first component of a two part adhesive or sealant composition. The functionalized compounds of formula II described hereinabove can be used alone as the first component of the two part adhesive or sealant or can be formulated into compositions. The concentrations of the components utilized to form the compositions will vary depending upon a number of factors, including the types and molecular weights of the particular components used and the desired end use application of the biocompatible composition, e.g., an adhesive or sealant. Generally, the composition may contain from about 25% to about 100% by weight, in embodiments from about 35% to about 90% by weight, of the previously described functionalized compounds of formula II.

If the viscosity of the functionalized compounds of the present disclosure is deemed too high for a particular application, emulsion compositions may be formulated that include a solvent in addition to the compounds. Suitable solvents or dispersants which may be utilized include, for example, polar solvents such as water, triethylene glycol, methoxy-polyethylene glycols, dimethylformamide, dimethylacetamide, gamma-butyrolactone, N-methylpyrrolidone, ketones such as methyl ethyl ketone, cyclohexanone, diethylene glycol monoethyl ether acetate, diethylene glycol monobutyl ether acetate, diethylene glycol monomethyl ether, diethylene glycol monoethyl ether, diethylene glycol monobutyl ether, diethylene glycol monoisobutyl ether, diisobutyl ketone, diacetone alcohol, ethyl amyl ketone, ethyl lactate, and the like, and mixtures thereof. In other embodiments, solvents such as tetrahydrofuran, ethyl acetate, isopropyl acetate, butyl acetate, isopropanol, butanol, acetone, mixtures thereof, and the like, may be utilized.

The amount of solvent(s) used will depend on a number of factors including the particular functionalized compound employed and the intended end use of the composition. Generally, the solvent will be from about 0 to about 90 weight percent of the entire composition, in embodiments from about 10 to about 80 weight percent of the entire composition. The use of one or more solvents can produce an emulsion having a viscosity of from about 50 cP to about 2000 cP, in embodiments from about 100 cP to about 1750 cP. Such emulsions can advantageously be sprayed using any suitable spraying device.

Where the functionalized compound includes isocyanate functionality and the solvent contains hydroxyl groups, the solvent is advantageously mixed with the functionalized compounds immediately prior to use to avoid undesired pre-gelling.

The second component of the two part adhesive or sealant may be a composition containing a multifunctional compound. Where the functionalized compound of the first component includes electrophilic groups, the second component should contain compounds with multiple nucleophilic groups. Where the functionalized compound of the first component includes nucleophilic groups, the second component should contain compounds with multiple electrophilic groups. Thus, in some embodiments, the multifunctional compounds of the second component of the two part sprayable adhesive or sealant contains about two to about six electrophilic groups such as, for example, —CO$_2$N(COCH$_2$)$_2$, —CO$_2$H, —CHO, —CHOCH$_2$, —N=C=O, —SO$_2$—CH=CH$_2$, —N(COCH)$_2$, —S—S—(C$_5$H$_4$N), and the like. In other embodiments, the multifunctional compounds of the second component of the two part sprayable adhesive or sealant contains about two to about six electrophilic groups such as, for example, —NH$_2$, —SH, —OH, —PH$_2$, —CO—NH—NH$_2$, and the like.

In particularly useful embodiments where the first component of the sprayable adhesive or sealant contains an isocyanate-functional compound of formula III, the second component of the two part adhesive or sealant contains a polyamine compound. Suitable polyamino functional compounds include, but are not limited to, ethylene diamine, hexamethylene diamine, lysine, putrescine(1,4-diaminobutane), spermidine(N-(3-aminopropyl)-1,4-butanediamine), spermine(N,N'-bis(3-aminopropyl)-1,4-butanediamine), isomers of hexamethylene diamine, diethylene triamine, triethylene tetramine, tetraethylene pentamine, bishexamethylene triamine, N,N'-bis(3-aminopropyl)-1,2-ethane diamine, N-(3-Aminopropyl)-1,3-propane diamine, N-(2-aminoethyl)-1,3 propane diamine, cyclohexane diamine, isomers of cyclohexane diamine, 4,4'-methylene biscyclohexane amine, 4'4'-methylene bis(2-methylcyclohexanamine), toluene diamine, phenylene diamine, isophorone diamine, and phenalkylene polyamines.

In another embodiment, the second component may contain a polyamino functional macromer compound, including polyoxyalkylene amines sold under the name JEFFAMINE® by Huntsman Performance Chemicals (Houston, Tex.), other amino-functionalized polyalkylene oxides, polypeptides including polypeptides having lysine and/or arginine residues, and the like.

The multifunctional compounds described hereinabove can be used alone as the second component of the two part adhesive or sealant or can be formulated into compositions. The concentrations of the components utilized to form the compositions will vary depending upon a number of factors, including the types and molecular weights of the particular components used and the desired end use application of the biocompatible composition, e.g., an adhesive or sealant. Generally, the multifunctional compounds may be present in the second component in amounts of from about 1% to about 50% by weight of the second component, in embodiments from about 5% to about 45% by weight of the second component, typically from about 10% to about 40% by weight of the second component.

Upon administration to tissue in situ, the functionalized compounds of the first component described hereinabove react with the multifunctional compounds of the second component thereby cross-linking to form a gel matrix that serves as an excellent tissue adhesive or sealant. Normally, the cross-linking reaction is conducted at temperatures ranging from about 20° C. to about 40° C., in embodiments from about 25° C. to about 35° C., for a period of time ranging from about 1 second to about 20 minutes, in embodiments from about 10 seconds to about 3 minutes.

A variety of optional ingredients may also be added to the compositions of the present disclosure. The optional ingredients may be included in the first component of the two part adhesive or sealant, in the second component of the two part adhesive or sealant, or in both components of the two part adhesive or sealant. For example, compositions in accordance with this disclosure may optionally include one or more catalysts. The addition of a catalyst can decrease the cure time of the compositions of the present disclosure. Catalysts which may be utilized include tertiary amine catalysts, quaternary amine catalysts, and the like.

Suitable tertiary amine catalysts which may be added include, but are not limited to, triethylenediamine, 4-methylmorpholine, N,N,N',N'',N''-pentamethyldiethylenetriamine, dimethylcyclohexylamine, N,N,N',N'-tetramethylethylenediamine, 1-[2-(Dimethylamino)ethyl]piperazine, 3-methoxy-N-dimethyl propyl amine, 4-ethylmorpholine, N,N-diethylethanolamine, N-coco morpholine, N,N-dimethyl-N', N'-dimethyl isopropyl-propylene diamine, N,N-diethyl-3-diethyl amino propyl amine, and dimethyl benzyl amine.

Suitable quaternary amine catalysts include, for example, lower alkyl ammonium halides and their derivatives such as hydroxy, chlorhydrin and epoxy substituted lower alkyl trimethylammonium halides such as substituted propyltrimethylammonium chlorides. Quaternary amines which may be utilized include dihydroxypropyltrimethylammonium chloride, chlorohydroxypropyltrimethylammonium chloride, and epoxypropyl-trimethylammonium chloride. Specific examples of the above compounds include 3-chloro-2-hydroxypropyl trimethyl ammonium chloride, 2,3-epoxypropyl trimethyl ammonium chloride, 3-chloro-2-hydroxypropyl trimethyl ammonium chloride, and 2,3-dihydroxypropyltrimethyl ammonium chloride.

In other embodiments, catalysts for use in the cross-linking reaction include stannous octoate, and the like.

The amount of catalyst employed can be from about 0.5 grams to about 50 grams per kilogram of the compound being cross-linked. In embodiments, the amount of catalyst can be from about 0.5 grams to about 10 grams per kilogram of the compound being cross-linked.

Other optional ingredients which may also be added to the compositions of the present disclosure include surfactants, antimicrobial agents, colorants, preservatives, imaging agents e.g., iodine, barium sulfate, or fluorine, or medicinal agents. In some embodiments, the present compositions may optionally contain one or more bioactive agents. The term "bioactive agent", as used herein, is used in its broadest sense and includes any substance or mixture of substances that have clinical use. Consequently, bioactive agents may or may not have pharmacological activity per se, e.g., a dye. Alternatively a bioactive agent could be any agent which provides a therapeutic or prophylactic effect, a compound that affects or participates in tissue growth, cell growth or cell differentiation, a compound that may be able to invoke a biological action such as an immune response, or a compound that could play any other role in one or more biological processes.

Examples of classes of bioactive agents which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Suitable antimicrobial agents which may be included as a bioactive agent in the present compositions include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the present compositions.

Other bioactive agents which may be included as a bioactive agent in the present compositions include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; antispasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anticancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the present compositions include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons ($\beta$-IFN, ($\alpha$-IFN and $\gamma$-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; and ribozymes.

Naturally occurring polymers, including proteins such as collagen and derivatives of various naturally occurring polysaccharides such as glycosaminoglycans, can optionally be incorporated into the compositions of the present disclosure as the bioactive agent.

A single bioactive agent may be utilized in the present compositions or, in alternate embodiments, any combination of bioactive agents may be utilized to form compositions of the present disclosure.

When the two components of the two part adhesive or sealant are applied to tissue either simultaneously or sequentially, they cross-link to form a gel matrix that serves as an excellent tissue adhesive or sealant. Normally, the cross-linking reaction is conducted at temperatures ranging from about 20° C. to about 40° C., in embodiments from about 25° C. to about 35° C., for a period of time ranging from about fifteen seconds to about 20 minutes or more typically about 30 seconds to about 3 minutes. The exact reaction conditions for achieving cross-linking of the compositions of the present disclosure may depend upon a variety of factors, including the functionality of the compounds, the degree of functionalization, the presence of a catalyst, the particular solvent present, if any, and the like.

The cross-linked compositions can be used in a medical/surgical capacity in place of, or in combination with, sutures, staples, clamps, and the like. In one embodiment, the present compositions can be used to seal or adhere delicate tissue together, such as lung tissue, in place of conventional tools that may cause mechanical stress. The present compositions can also be used to seal air and/or fluid leaks in tissue as well as to prevent post-surgical adhesions and to fill voids and/or defects in tissue.

Where the composition is intended for delivery of a bioactive agent such as a drug or protein, the amounts of the compounds of the present disclosure can be adjusted to promote the initial retention of the drug or polymer in the bioabsorbable composition and its subsequent release. Methods and means for making such adjustments will be readily apparent to those skilled in the art.

The compositions of the present disclosure can be used for a number of different human and animal medical applications including, but not limited to, wound closure (including surgical incisions and other wounds). Adhesives may be used to bind tissue together either as a replacement of, or as a supplement to, sutures, staples, tapes and/or bandages. Use of the present compositions can eliminate or substantially reduce the number of sutures normally required during current practices, and eliminate the subsequent need for removal of external staples and certain types of sutures. The compositions described herein can thus be particularly suitable for use with delicate tissues where sutures, clamps or other conventional tissue closure mechanisms may cause further tissue damage.

To effectuate the joining of two tissue edges, the two edges are approximated, and the two components of the two part adhesive or sealant are applied to tissue either simultaneously or sequentially to the two approximated edges. The composition crosslinks rapidly, generally taking less than one minute. Compositions of the present disclosure can thus be applied to the wound and allowed to set, thereby closing the wound.

While certain distinctions may be drawn between the usage of the terms "flesh" and "tissue" within the scientific community, the terms are used interchangeably herein as referring to a general substrate upon which those skilled in the art would understand the present bioabsorbable composition to be utilized within the medical field for the treatment of patients. As used herein, "tissue" may include, but is not limited to, skin, bone, neuron, axon, cartilage, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic and/or ascite tissue.

The compositions described herein can also be used as sealants. When used as a sealant, a two part sealant composition of the present disclosure can be used in surgery to form a bioabsorbable composition to prevent or inhibit bleeding or fluid leakage both during and after a surgical procedure. It can also be applied to prevent air leaks associated with pulmonary surgery. Compounds herein may be applied directly to the desired area in at least an amount sufficient to seal off any defect in the tissue and seal off any fluid or air movement. The two part adhesive or sealant may also be used to prevent or control blood or other fluid leaks at suture or staple lines.

The present two part adhesive or sealant also can be used to attach skin grafts and position tissue flaps during reconstructive surgery. Alternatively, the present two part adhesive or sealant can be used to close tissue flaps in periodontal surgery.

Application of the two part adhesive or sealant of the present disclosure can be done by any conventional means. These include dripping, brushing, or other direct manipulation of the compositions on the tissue surface, or spraying of the compositions onto the surface. In open surgery, application by hand, forceps or the like is contemplated. In endoscopic surgery, the compositions can be delivered through the cannula of a trocar, and spread at the site by any device known in the art. It should be understood that the two components should be stored in separate containers until application or just prior thereto to avoid pre-mature crosslinking. Keeping the two components refrigerated may also assist in preventing unwanted crosslinking.

In some embodiments, the first component and the second components are delivered from an apparatus having a first chamber containing the first component and a second chamber containing the second component of a two part adhesive or sealant, and at least one outlet for dispensing the first and second components. In some useful embodiments, the first component includes a functionalized compound of formula II and the second composition includes a multifunctional compound.

In other embodiments, especially where the two part adhesive or sealant of the present disclosure is to be utilized as a void filler or sealant to fill a defect in an animal's body, it may be advantageous to more precisely control the conditions and extent of cross-linking. For example, it may be desirable to partially cross-link the two part adhesive or sealant prior to use to fill a void in animal tissue. In embodiments, the two components may be mixed prior to dispensing. In such a case the two part adhesive or sealant of the present disclosure can be applied to the void or defect and allowed to set, thereby filling the void or defect.

In another embodiment, the present disclosure is directed to a method for using the two part adhesive or sealant of the present disclosure to adhere a medical device to tissue. The medical device may include an implant. Other medical devices include, but are not limited to, pacemakers, stents, shunts and the like. Generally, for adhering a device to the surface of animal tissue, a composition of the present disclosure can be applied to the device, to the tissue surface, or to both. The device and tissue surface are then brought into contact with the two part adhesive or sealant therebetween. Once the two part adhesive or sealant crosslinks and sets, the device and tissue surface are effectively adhered to each other.

The two part adhesive or sealant of the present disclosure can also be used to prevent post surgical adhesions. In such an application, the two part adhesive or sealant of the present disclosure is applied and cured to form a layer on surfaces of internal tissues in order to prevent the formation of adhesions at a surgical site during the healing process.

The two part adhesive or sealant has a number of advantageous properties. The two part adhesive or sealant compositions of the present disclosure are safe, possess enhanced adherence to tissue, are biodegradable, have enhanced hemostatic potential, have low cost, and are easy to prepare and use. By varying the selection of the compounds utilized to form the two part adhesive or sealant, the strength and elasticity of the resulting gel can be controlled, as can the gelation time.

The present two part adhesive or sealant compositions rapidly form a compliant gel matrix as the bioabsorbable composition, which insures stationary positioning of tissue edges or implanted medical devices in the desired location and lowers overall required surgical/application time. The resulting gel exhibits little or no swelling upon gel matrix formation, and therefore retains the positional integrity of the aligned tissue edges and/or location of a medical device. The two part adhesive or sealant forms strong cohesive bonds. It exhibits excellent mechanical performance and strength, while retaining the necessary pliability to adhere living tissue. This strength and pliability allows a degree of movement of tissue without shifting the surgical tissue edge.

In order that those skilled in the art may be better able to practice the features of the present disclosure described herein, the following examples are provided to illustrate, but not limit, the features of the present disclosure.

EXAMPLE 1

Forty one grams of a random glycolide/lactide copolymer containing 18% glycolide was added into a 3 neck 250 ml round bottom flask equipped with a mechanical mixer under a nitrogen blanket and the flask was then placed into an oil bath. The oil bath temperature was set to 155° C. After the copolymer melted, 59.0 g of PEG 400 (Aldrich; Milwaukee, Wis.) and 0.04 g of stannous octoate (Aldrich; Milwaukee, Wis.) were added. The reaction was allowed to proceed at 155° C. for 24 hours. The final product had a viscosity of 825 cps at 25° C. as measured using a Brookfield cone and plate viscometer at a shear rate of 10 sec$^{-1}$. The structure was confirmed by NMR and FTIR (Spectra) to be:

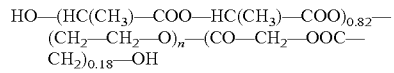

EXAMPLE 2

58.16 grams of a random glycolide/lactide copolymer containing 18% glycolide was added into a 3 neck 250 ml round bottom flask equipped with a mechanical mixer under a nitrogen blanket and the flask was then placed into an oil bath. The oil bath temperature was set to 155° C. After the copolymer melted, 41.84 g of PEG 200 (Aldrich; Milwaukee, Wis.) and 0.04 g of stannous octoate (Aldrich; Milwaukee, Wis.) were added. The reaction was allowed to proceed at 155° C. for 24 hours. The final product had a viscosity of 1429 cps at 25° C. as measured using a Brookfield cone and plate viscometer at a shear rate of 10 sec$^{-1}$. The structure was confirmed by NMR and FIR (Spectra) to be:

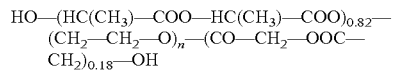

EXAMPLE 3

27.54 grams of a random glycolide/ϵ-caprolactone copolymer containing 10% glycolide was added into a 3 neck 250 ml round bottom flask equipped with a mechanical mixer under a nitrogen blanket and the flask was placed into an oil bath. The oil bath temperature was set to 155° C. After the copolymer melted, 72.46 g of PEG 600 (Aldrich) and 0.04 g of stannous octoate (Aldrich; Milwaukee, Wis.) are added. The reaction was allowed to proceed at 155° C. for 24 hours. The final product had a viscosity ranging from 2415-2374 cps at 25° C. as measured using a Brookfield cone and plate viscometer at a shear rate of 10 sec$^{-1}$. The structure was confirmed by NMR and FFIR (Spectra) to be:

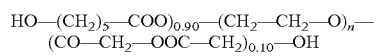

EXAMPLE 4

Ten grams of a random glycolide/lactide copolymer containing 18% glycolide were added into a round bottom flask under a nitrogen blanket. To this, 24.85 g of hexamethylene diisocyanate (Aldrich; Milwaukee, Wis.) were added with stirring at room temperature. The reaction mixture was heated to 120° C. and the reaction allowed to continue for 24 hours. The product was recovered and unreacted materials were extracted in petroleum ether. After decanting excess solvent, the precipitate was dried under vacuum. The resulting product had a viscosity of 110 cps at 25° C. as measured using a Brookfield cone and plate viscometer at a shear arte of 10 sec$^{-1}$. The isocyanate content was 25.2% as measured by titration on a TitroLine Alpha Autotitrator manufactured by Schott Geräte GmbH, Mainz, Germany using a modification of ASTM D 2572-91 to accommodate use of an autotitrator.

EXAMPLE 5

Ten grams of the product from Example 2 were added into a round bottom flask under a nitrogen blanket. To this 35.6 g of hexamethylene diisocyanate (Aldrich; Milwaukee, Wis.) were added with stirring at room temperature using a magnetic stirrer. The reaction mixture was heated to 120° C. and the reaction allowed to continue for 24 hours. The product was recovered and unreacted materials were extracted in petroleum ether. After decanting excess solvent, the precipitate was dried under vacuum. The resulting product had a viscosity of 477.7 cps at 25° C. as measured using a Brookfield cone and plate viscometer at a shear arte of 10 sec$^{-1}$. The isocyanate content was 17.6%.

EXAMPLE 6

Ten grams of the product from Example 3 were added into a round bottom flask under a nitrogen blanket. To this 29.4 g of hexamethylene diisocyanate (Aldrich; Milwaukee, Wis.) were added with stirring at room temperature using a magnetic stirrer. The reaction mixture was heated to 120° C. and the reaction continued for 24 hours. The product was recovered and unreacted materials were extracted in petroleum ether. After decanting excess solvent, the precipitate was dried under vacuum. The resulting product had a viscosity of 255 cps at 25° C. as measured using a Brookfield cone and plate viscometer at a shear rate of 10 sec$^{-1}$. The isocyanate content was 16.6%.

It will be understood that various modifications may be made to the embodiments disclosed herein. Therefore the above description should not be construed as limiting, but merely as exemplifications of preferred embodiments. Those skilled in the art will envision other modifications within the scope and spirit of the claims appended hereto.

What is claimed is:

1. A compound of the formula:

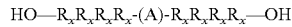

wherein A is a group derived from a dihydroxy compound with a molecular weight of less than about 1000; R can be the same or different at each occurrence and comprises groups derived from a compound selected from the group consisting of glycolide, lactide, p-dioxanone, trimethylene carbonate, and combinations thereof; and x can be the same or different at each occurrence and is 0 or 1, provided that at least two R groups are present.

2. A compound as in claim 1 wherein A is a group derived from a polyalkylene oxide.

3. A compound as in claim 1 wherein A is a group derived from a polyethylene glycol compound having a molecular weight selected from the group consisting of about 200, about 400, about 600 and about 900.

4. A compound as in claim 1 wherein at least one R group is derived from glycolide and at least one other R group is derived from lactide.

5. A compound as in claim 1 having a formula selected from the group consisting of:

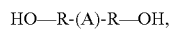

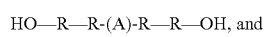

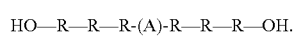

6. A method comprising reacting a compound of claim 1 with a diisocyanate.

7. A method as in claim 6 wherein the diisocyanate is selected from the group consisting of aromatic diisocyanates, aliphatic diisocyanates, and alicyclic diisocyanates.

8. A method as in claim 6 wherein the diisocyanate is selected from the group consisting of 2,4-toluene diisocyanate, 2,6-toluene diisocyanate, 2,2'-diphenylmethane diisocyanate, 2,4'-diphenylmethane diisocyanate, 4,4'-diphenylmethane diisocyanate, diphenyldimethylmethane diisocyanate, dibenzyl diisocyanate, naphthylene diisocyanate, phenylene diisocyanate, xylylene diisocyanate, 4,4'-oxybis(phenylisocyanate), tetramethylxylylene diisocyanate, tetramethylene diisocyanate, hexamethylene diisocyanate, lysine diisocyanate, 2-methylpentane-1,5-diisocyanate, 3-methylpentane-1,5-diisocyanate, 2,2,4-trimethylhexamethylene diisocyanate, isophorone diisocyanate, cyclohexane diisocyanate, hydrogenated xylylene diisocyanate, hydrogenated diphenylmethane diisocyanate, hydrogenated trimethylxylylene diisocyanate, and 2,4,6-trimethyl 1,3-phenylene diisocyanate.

9. A method comprising reacting a compound of claim 1 with a succinimidyl ester selected from the group consisting of sulfosuccinimidyl esters and N-hydroxysuccinimidyl esters.

10. A compound of the formula:

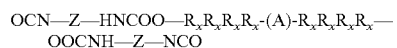

wherein Z is an aromatic or aliphatic group; A is a group derived from a polyalkylene oxide with a molecular weight of less than about 1000; R can be the same or different at each occurrence and comprises groups derived from absorbable monomers selected from the group consisting of glycolide, lactide, p-dioxanone, trimethylene carbonate, and combinations thereof; and x can be the same or different at each occurrence and is 0 or 1, provided that at least two R groups are present.

11. A compound as in claim 10 wherein Z is selected from the group consisting of toluene, diphenylmethane, diphenyldimethylmethane, dibenzyl, naphthylene, phenylene, xylylene, oxybisphenyl, tetramethylxylylene, tetramethylene, hexamethylene, lysine, methylpentane, trimethylhexamethylene, isophorone, cyclohexane, hydrogenated xylylene, hydrogenated diphenylmethane, hydrogenated trimethylxylylene, trimethylphenylene, and combinations thereof.

12. A compound as in claim 10 wherein A is a group derived from a polyethylene glycol having a molecular weight selected from the group consisting of about 200, about 400, about 600 and about 900.

13. A compound of the formula:

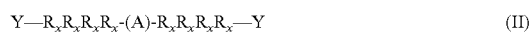

wherein Y is a group providing electrophilic or nucleophilic functionality; A is a group derived from a dihydroxy compound with a molecular weight of less than about 1000; R can be the same or different at each occurrence and comprises groups derived from absorbable monomers selected from the group consisting of glycolide, lactide, p-dioxanone, trimethylene carbonate, and combinations thereof; and x can be the same or different at each occurrence and is 0 or 1, provided that at least two R groups are present.

14. A compound as in claim 13 wherein Y includes a group selected from the group consisting of —NH$_2$, —SH, —OH, —PH$_2$, —CO—NH—NH$_2$, —CO$_2$N(COCH$_2$)$_2$, —CO$_2$H, —CHO, —CHOCH$_2$, —N═C═O, —SO$_2$—CH═CH$_2$, —N(COCH)$_2$, —S—S—(C$_5$H$_4$N), and combinations thereof.

15. A compound as in claim 13 wherein Y comprises an isocyanate.

16. A two part adhesive system comprising a first composition including a compound of claim 13 and a second composition comprising a multifunctional compound.

17. A two part adhesive system comprising a first composition comprising a compound of claim 13 and a second composition comprising a polyamine compound.

18. A method comprising
providing a dispensing device having at least two chambers and at least one outlet;
providing a first composition including a compound of claim 13 in a first chamber of the dispensing device;
providing a second composition including a multifunctional compound in a second chamber of the dispensing device; and
dispensing the first and second compositions through the at least one outlet of the dispensing device.

19. A method as in claim 18 wherein the second composition comprises a polyamine compound.

20. A method as in claim 18 further comprising the step of mixing the first and second compositions prior to dispensing.

21. A compound of the formula:

$$HO-R_xR_xR_xR_x-(A)-R_xR_xR_xR_x-OH$$

wherein A is a group derived from a dihydroxy compound with a molecular weight of less than about 1000; R can be the same or different at each occurrence and comprises groups derived from a compound selected from the group consisting of glycolide, lactide, p-dioxanone, trimethylene carbonate, and combinations thereof; x can be the same or different at each occurrence and is 0 or 1, provided that at least two R groups are present; and wherein the compound has a viscosity of from about 1,000 to about 500,000 centipoise at a temperature of from about 0° C. to about 40° C.

* * * * *